United States Patent [19]

Bianco

[11] Patent Number: 5,314,481
[45] Date of Patent: May 24, 1994

[54] HINGED KNEE PROSTHESIS WITH EXTENDED PATELLAR TRACK

[75] Inventor: Peter T. Bianco, Memphis, Tenn.

[73] Assignee: Wright Medical Technology, Inc., Arlington, Tenn.

[21] Appl. No.: 974,549

[22] Filed: Nov. 12, 1992

[51] Int. Cl.[5] ............................................. A61F 2/38
[52] U.S. Cl. ........................................................ 623/20
[58] Field of Search ............................. 623/16, 18, 20

[56] References Cited

U.S. PATENT DOCUMENTS

| | | | |
|---|---|---|---|
| 3,996,624 | 12/1976 | Noiles | 623/20 |
| 4,262,368 | 4/1981 | Lacey | 623/20 |
| 5,011,496 | 4/1991 | Forte | 623/20 |

FOREIGN PATENT DOCUMENTS

| | | | |
|---|---|---|---|
| 2244064 | 3/1974 | Fed. Rep. of Germany | 623/20 |
| 2129306 | 5/1984 | United Kingdom | 623/20 |

*Primary Examiner*—David Isabella

[57] ABSTRACT

A knee prosthesis includes a femoral component for attachment to the condyle region of a femur in a human knee and a tibial component for attachment to the superior articular region of a tibia in the knee. The femoral component and tibial component are pivotally hinged together by a pintle. The femoral component includes a concave channel extending perpendicular to the axis of the pintle to form a patellar guide surface.

6 Claims, 5 Drawing Sheets

HINGED KNEE PROSTHESIS WITH EXTENDED PATELLAR TRACK

TECHNICAL FIELD

The subject invention relates to a prosthesis for replacement of a human knee joint, and more particularly to such a knee prosthesis having femoral and tibial components hinged to one another about a definite pivotal axis and including a patella guide track.

BACKGROUND OF THE INVENTION

The knee is generally regarded as being one of the most inherently unstable joints in the human body due in part to the complex, interrelated motions to which the knee is subjected during normal motion. In the past, various mechanical approaches have been proposed in an attempt to approximate the natural action of the knee through artificial total joints However, advanced conditions of disease or serious traumatic injury to the knee joint complicate surgical repair and efforst to simulate the natural knee motion through the use of a prosthesis.

Under circumstances where the knee is beyond acceptable repair using conventional total joint reconstruction with separated condylar type or posterior stabilized prostheses as the articular femoral and tibial surfaces, it has become acceptable practice to reconstruct the knee with a hinged type prosthesis. For example, U.S. Pat. No. 4,262,368 in the name of Lacey, issued Apr. 21, 1981 and assigned to the assignee of the subject invention, discloses a prosthesis for replacement of the human knee joint having articulating femoral and tibial components hingedly connected about a transverse, or medial-lateral axis. The Lacey prosthesis provides appropriate constraint while allowing for rotation and distraction during knee motion. This minimizes prosthetic and/or fixation failure by reducing torsional and tensile stresses The Lacey prosthesis also includes a patellar track formed in the femoral component as a central concave groove. The patellar track provides a contact surface for proximal-distal movement and positioning of the patella, either natural patella or prosthetic patella, during knee flexure.

The primary disadvantage of this Lacey prosthesis is manifest when the natural patella remains in the knee joint after surgical implantation of the knee prosthesis. The natural patella is salvaged in a significant number of pediatric applications. As shown in FIG. 1, when the knee is flexed at or near its maximum, there is a possibility that the patellar track may exceed by relative movement, i.e., overrun, the patella. In these situations, it is possible that the superior edge of the patella will become snagged, or lodged, in the hinge joint below the patellar track. Under these circumstances, an extremely painful locked knee condition occurs.

SUMMARY OF THE INVENTION AND ADVANTAGES

The subject invention is a total artificial knee joint comprising a femoral component for implantation on a prepared surface of the distal femur, a tibial component for implantation on a prepared surface of the proximal tibia, and a hinge means interconnecting the femoral component and tibial component for pivoting the tibial component relative to the femoral component means throughout a predetermined arc about a medial-lateral pivotal axis. A patellar tracking means forms a patella guide surface disposed anteriorly to the pivotal axis and extending continuously and uninterrupted inferior to the pivotal axis throughout the predetermined arc thereby preventing the superior edge of a patella in a fully flexed knee from becoming painfully lodged in the hinge means or the interface between the femoral component means and the tibial component.

In other words, the subject invention overcomes the prior art disadvantages by the patellar tracking means forming the patella guide surface below the pivotal axis of the hinge means to prevent the patella from becoming painfully snagged between the tibial and femoral components. The subject patella guide surface extends continuous and uninterrupted below, or inferior of, the pivotal axis throughout the predetermined arc of pivotal movement. Thus, in the subject invention, the painful locked knee condition possible with prior art prostheses is positively avoided since the patella is supported at all possible flexed positions of the knee.

BRIEF DESCRIPTION OF THE DRAWINGS

Other advantages of the present invention will be readily appreciated as the same becomes better understood by reference to the following Detailed Description when considered in connection with the accompanying Drawings wherein.

DETAILED DESCRIPTION

Figure 2:
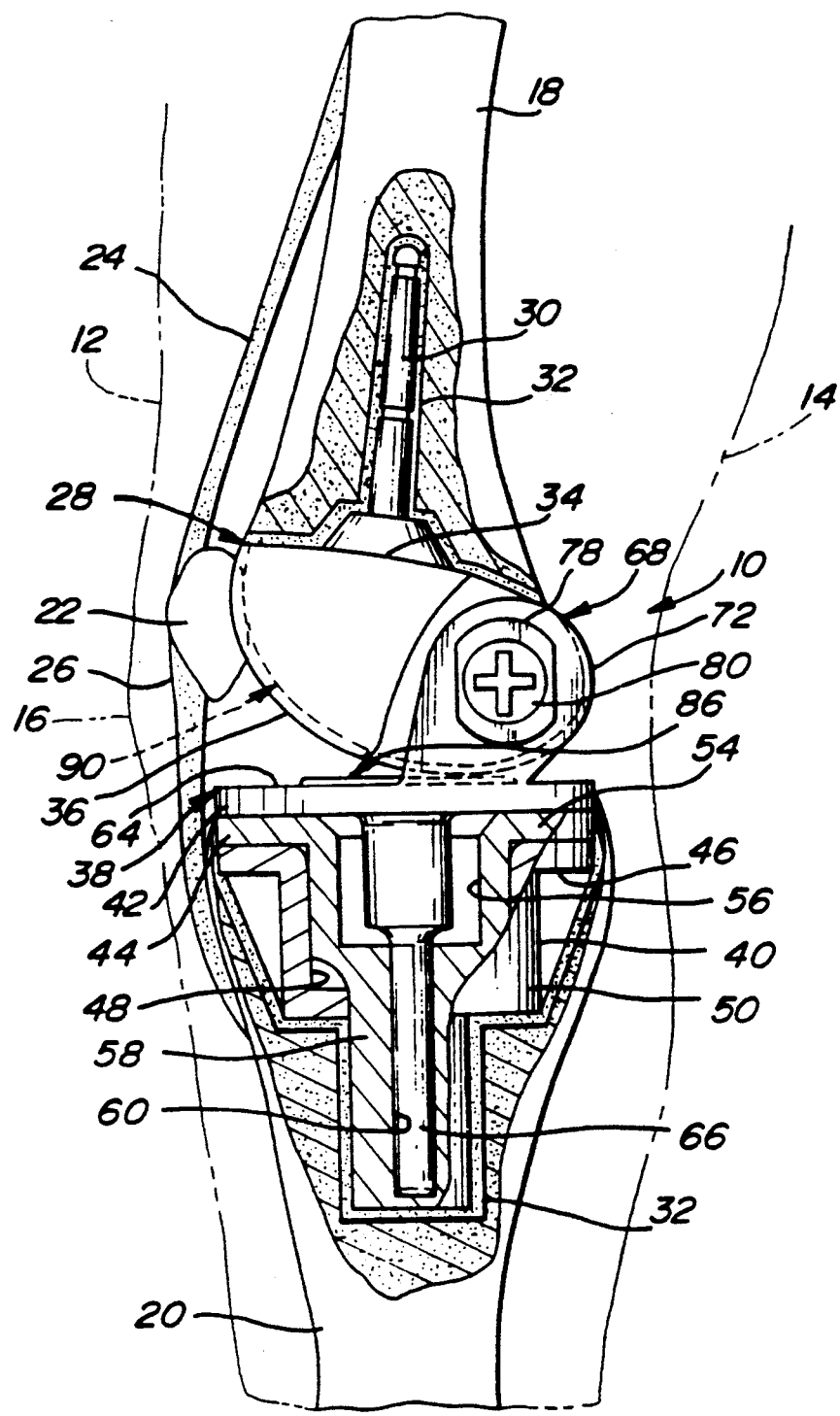
FIG. 2 is a simplified sectional view of a human right knee implanted with a prosthesis according to the invention.
Figure 3:
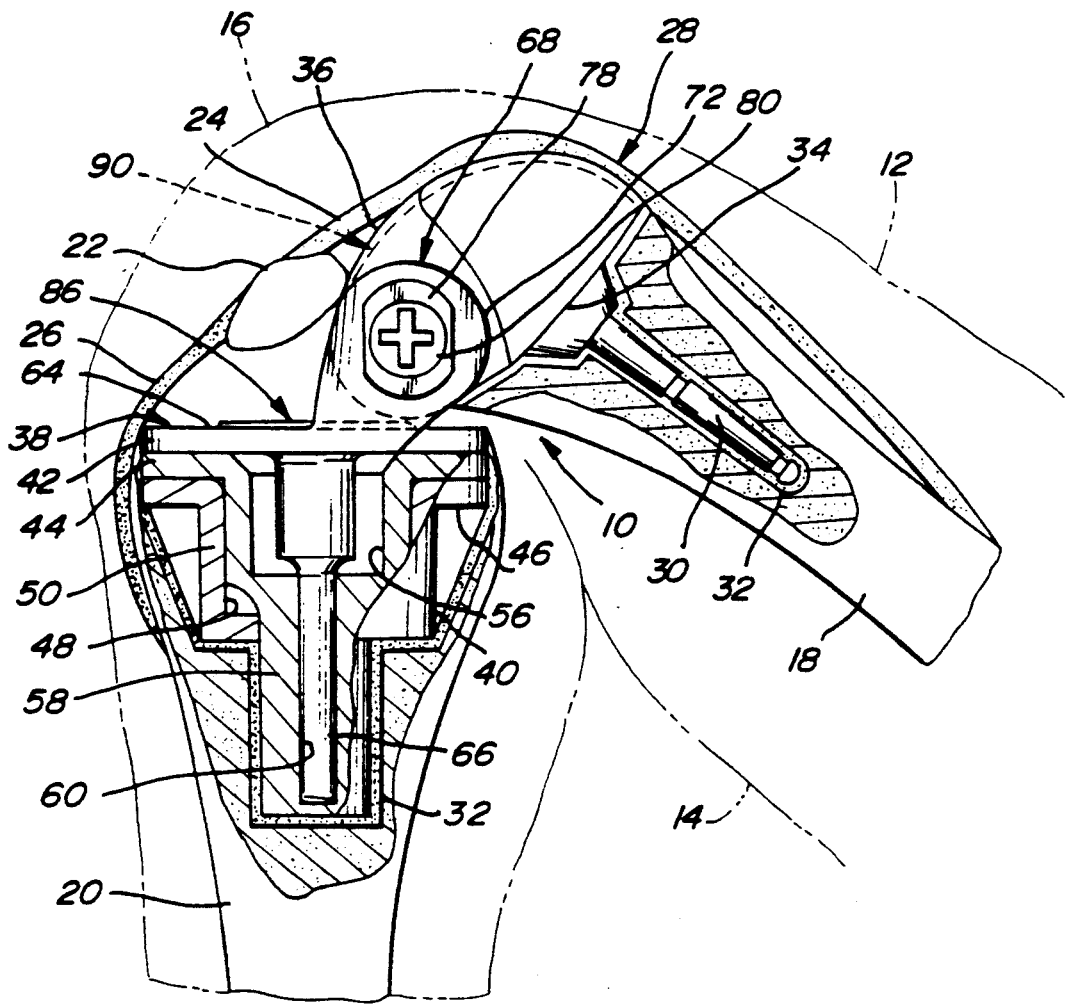
FIG. 3 is a sectional view as in FIG. 2 with the knee pivoted at or near the position of maximum flexure.
Figure 4:
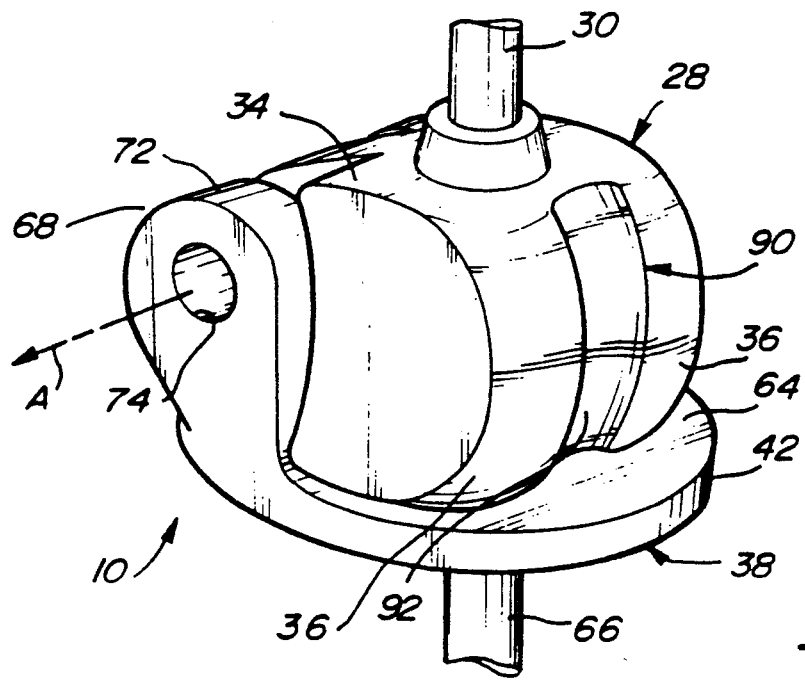
FIG. 4 is a simplified perspective view of the prosthesis of the subject invention.
Figure 5:
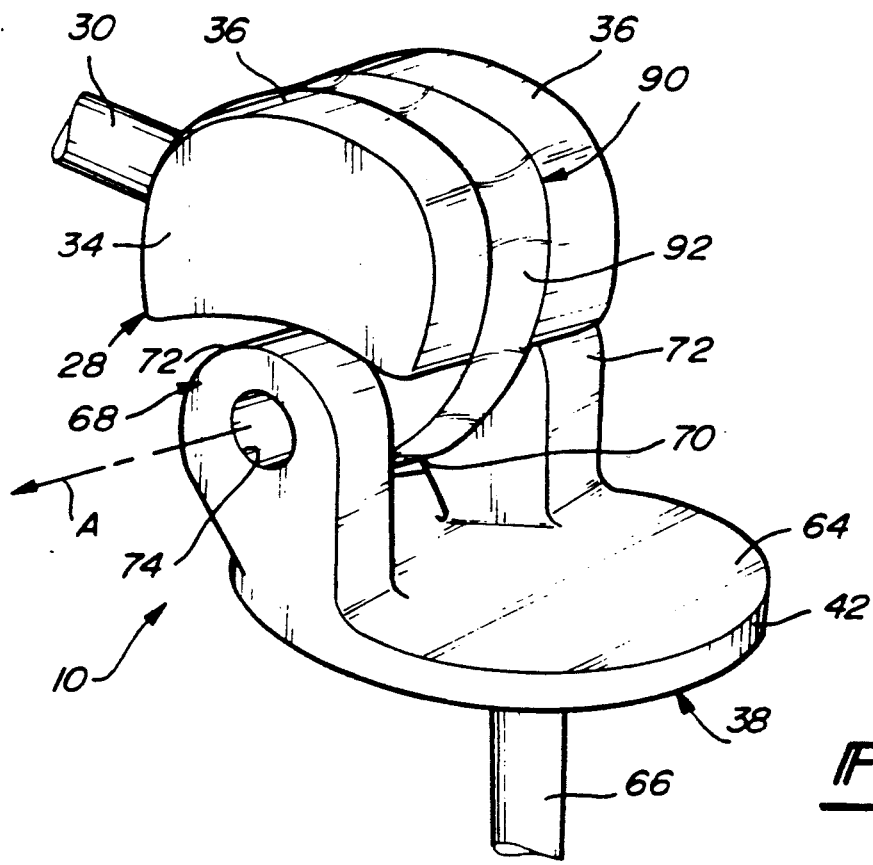
FIG. 5 is a perspective view as in FIG. 4 with the femoral component pivoted approximately 90°.
Figure 6:
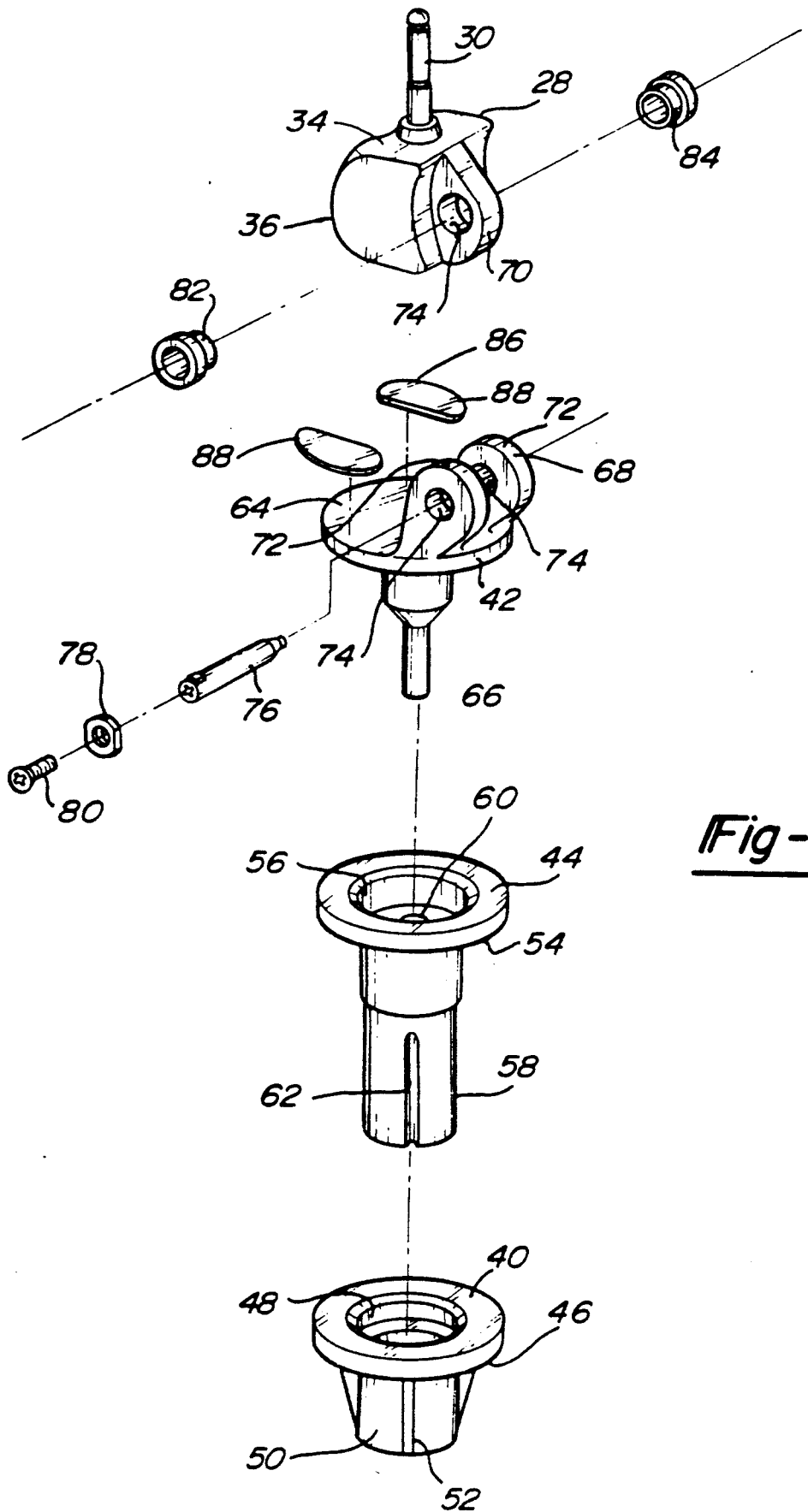
FIG. 6 is an exploded perspective view of the subject prosthesis.

Referring to FIGS. 2-6, wherein like numerals indicate like or corresponding parts throughout the several views, a total knee joint prosthesis according to the subject invention is generally shown at 10. In FIGS. 2 and 3, the knee region of a human right leg is shown in phantom including an anterior region 12, a posterior region 14, a knee 16, a femur 18, and a tibia 20. A patella 22 is disposed anteriorly of the condyles and connected to the quadriceps muscle by a tendon of the quadriceps femoris 24 and to the tibia 20 by a ligamentum patellae 26.

The prosthesis 10 includes a femoral component means, generally indicated at 28, for fixed attachment to the condyle region of the femur 18. The femoral component preferably includes an elongated stem 30 constructed and adapted for intramedullary implantation in the distal femur 18 and is of sufficient length to provide secure implantation. As shown in FIGS. 2 and 3, a conventionally used adhesive bone cement 32 provides further attachment for the stem 30 in an axially drilled and reamed bore in the femur 18. The femoral component means 28 also includes a base member 34 fixedly connected to the stem 30. The base member 34 includes a curved anterior and inferior surface 36 forming the prosthetic condyle surfaces 36 of the femur 18.

The prosthesis 10 further includes a tibial component, generally indicated at 38, for fixed attachment to the superior articulator region of the tibia 20. The tibial component 38 is substantially similar to that disclosed in U.S. Pat. No. 4,262,368, issued in the name of Lacey, the entire disclosure of which is incorporated herein by reference and relied upon. Specifically, the tibial component 38 includes a metal base or tray 40, a proximal metal plateau member 42, and an intermediate bushing insert 44 formed, for example, of polyethylene an equivalent non-abrading synthetic plastic material. The base 40 is cup-shaped in configuration and includes an outer flange 46 surrounding an internal cup-shaped recess 48 from which extends distally a tubular body 50 having ridges 52 which extend longitudinally in a proximal-distal direction and, after implantation, prevent rotation of the base 40 in the prepared tibia 20.

The intermediate bushing 44 comprises a proximally located flange 54 constructed and adapted to be snugly positioned within the cup-shaped recess 48 of the base 40 and which surrounds a cup-shaped recess 56 in the proximal end of the intermediate bushing 44. An elongated tubular part 58, having a central opening 60 along its length, extends distally from the inner periphery of the flange 54 and is snugly received within the central opening in the base 40. A plurality of recesses 62 are formed in the outer surface of the tubular part 58 and extend longitudinally thereof for receiving correspondingly shaped projections on the inner wall of the base 40 to prevent relative rotational movement the two parts.

The plateau member 42 includes a circular flat metal plate 64 adapted to rest on the superior surface of the flange 54 of the bushing 44 and provided with an elongated integrally formed post 66 extending inferiorly, or downwardly, from the lower surface of the plate 64 in concentric relation thereto The post 66 is rotatably received into the central opening 60 of the intermediate bushing 44 for permitting free rotation between the platen member 42 and the intermediate bushing 44.

The knee joint 10 further includes a hinge means, generally indicated at 68, interconnecting the femoral component means 28 and the tibial component 38 for pivoting the components relative to one another throughout a predetermined arc of travel about a definite pivotal axis A. The predetermined arc may be as great or greater than 150°. The pivotal axis A extends horizontally and is disposed between the base member 34 of the femoral component means 28 and the plate 64 of the tibial component 38.

More particularly, the hinge means 68 includes a central knuckle 70 extending integrally from the base member 34 of the femoral component means 28, and a pair of flanking knuckles 72 disposed on opposite, i.e., medial and lateral, sides of the central knuckle 70. The flanking knuckles 72 extend integrally from the plate 64 of the tibial component 38. A bore 74 extends horizontally through the central 70 and flanking 72 knuckles along the pivotal axis A.

A pintle 76 of the well known type is secured in the bore 74 along the pivotal axis A for pivotally connecting the knuckles 70, 72. The hinge means 78 also includes a core 78 and a locking screw 80 for securing the pintle 76 and the bore 74 together, in the well known manner. The central knuckle 70 is constructed and adapted to receive from its two ends two tubular bushings 82, 84 which are formed of a synthetic plastic material and which provide a continuous opening having an internal diameter equal to the outer diameter of pintle 76.

A cushioning means, generally indicated at 86, is provided for cushioning impact between the condyle surfaces 36 of the femoral component means 28 and the superior surface of the plate 64 of the tibia attachment means 38 during flexing movement of the prosthesis 10. The cushioning means comprises bumpers 88 positioned on the plateau member 44. These bumpers 88 are formed of any non-metallic material capable of absorbing impact in a satisfactory manner, and are preferably embedded in recesses formed in the plateau member 42.

Figure 1:
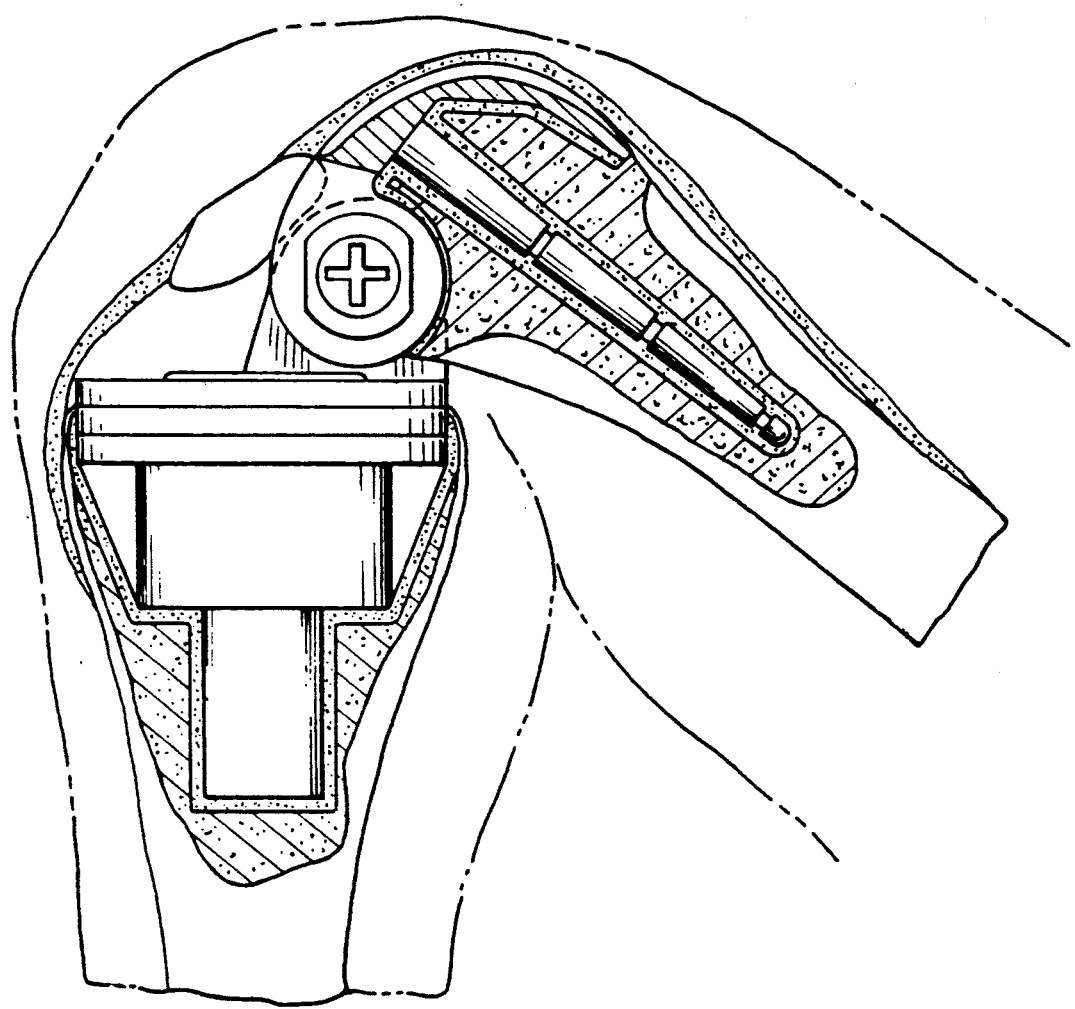
FIG. 1 is a simplified sectional view of a human right knee implanted with a prosthesis according to the prior art and exhibiting a "locked knee" condition.

The improvement of the subject prosthesis 10 comprises a patellar tracking means, generally indicated at 90 in FIGS. 2 through 5, for forming a patella guide surface 92 disposed anterior to the pivotal axis A. The patella guide surface 92 extends continuously and uninterrupted inferior of the pivotal axis A throughout the predetermined arc of movement. By extending the patella guide surface 92 below the pivotal axis A, the superior edge of the patella 22 in a fully flexed knee 16 is prevented from becoming painfully lodged in the hinge means 68 or within the interface between the femoral component means 28 and the tibial component 38, such as illustrated in FIG. 1. That is, the subject prosthesis 10 eliminates the painful condition made possible by the structure of prior art knee prostheses by extending the patella guide surface 92 below the pivotal axis A of the hinge means 68 throughout the full range of movement in the knee 16. Therefore, as the knee 16 is flexed and the prosthesis 10 is pivoted throughout its predetermined arc, the patellar tracking means 90 continuously guides and supports the patella 22 thereby preventing it from becoming being caught in the hinge means or wedged between the base member 34 and the plate 64.

The patella guide surface 92 extends anteriorly and superiorly from the central knuckle 70 and forms a concave, or substantially dished, channel perpendicular to the pivotal axis A. The condyle surfaces 36 are disposed on opposite, medial and lateral, sides of the patella guide surface 92. Thus, the patella guide surface 92 is aligned vertically with the central knuckle 70 and continuously supports the patella 22 anterior of the pivotal axis A. As best shown in FIG. 3, when the knee 16 is fully flexed, the patella 22 remains continuously supported and guided by the patella guide surface 92 so that the patella never disconnects from, or overruns, the patella guide surface 92. Thus, there is no way for the patella 22 to become accidently wedged in the hinge means 68 thereby causing the painful condition known colloquially as locked knee (FIG. 1). The subject prosthesis 10 is also structurally simple and efficient, thereby providing advantageous results over the prior art without unduly complicating the design. Further, implantation procedures are identical to those of the prior art, thereby simplify education of the surgical profession.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A total knee joint prosthesis comprising: femoral attachment means for fixed attachment to the condyle region of a femur in a human knee; tibial attachment means for fixed attachment to the superior articular region of a tibia in the knee; hinge means interconnecting the femoral attachment means and the tibial attachment means for pivoting the tibial attachment means relative to the femoral attachment means throughout a predetermined arc about a pivotal axis; and patellar tracking means for forming a patella guide surface disposed anterior the pivotal axis and extending continuously and uninterrupted inferior the pivotal axis throughout the predetermined arc thereby preventing the superior edge of a patella in a fully flexed knee from becoming painfully lodged in the hinge means or the interface between the femoral attachment means and the tibial attachment means; the hinge means comprising a central knuckle extending from the femoral attachment means and a pair of flanking knuckles disposed on opposite sides of the central knuckle and extending from the tibial attachment means, and the patella guide surface extends anteriorly and superiorly in aligned fashion from the central knuckle.

2. A prosthesis as set forth in claim 1 wherein the patella guide surface includes a concave channel extending perpendicular to the pivotal axis.

3. A prosthesis as set forth in claim 2 further including a bore extending through the central and flanking knuckles and a pintle secured in the bore.

4. A prosthesis as set forth in claim 3 further including a bushing disposed between the central and flanking knuckles.

5. A prosthesis as set forth in claim 4 wherein tibial attachment means includes a plate connected to the flanking knuckles, and a post extending inferior the plate.

6. A prosthesis as set forth in claim 5 wherein the femoral attachment means includes a pair of condyle surfaces disposed adjacent the central knuckle and on opposite sides of the patella guide surface.

* * * * *